(12) United States Patent
Fabian et al.

(10) Patent No.: US 10,251,567 B2
(45) Date of Patent: Apr. 9, 2019

(54) METHOD FOR AN ACCURATE AUTOMATED NON-INVASIVE MEASUREMENT OF BLOOD PRESSURE WAVEFORM AND APPARATUS TO CARRY OUT THE SAME

(71) Applicants: CZECH TECHNICAL UNIVERSITY IN PRAGUE, FACULTY OF ELECTRICAL ENGINEERING, Prague (CZ); CZECH TECHNICAL UNIVERSITY IN PRAGUE, CZECH INSTITUTE OF INFORMATICS, ROBOTICS, Prague (CZ)

(72) Inventors: Vratislav Fabian, Prague (CZ); Vaclav Kremen, Prague (CZ); Martin Dobias, Ricany (CZ)

(73) Assignees: Czech Technical University in Prague, Faculty of Electrical Engineering, Prague (CZ); Czech Technical University in Prague, Czech Institute of Informatics, Robotics and Cybernetics, Prague (CZ)

( * ) Notice: Subject to any disclaimer, the term of this patent is extended or adjusted under 35 U.S.C. 154(b) by 224 days.

(21) Appl. No.: 15/401,338

(22) Filed: Jan. 9, 2017

(65) Prior Publication Data
US 2017/0196468 A1 Jul. 13, 2017

(30) Foreign Application Priority Data
Jan. 7, 2016 (CZ) .......................................... 2016-6

(51) Int. Cl.
*A61B 5/0225* (2006.01)
*A61B 5/0235* (2006.01)
(Continued)

(52) U.S. Cl.
CPC ........ *A61B 5/02108* (2013.01); *A61B 5/0225* (2013.01); *A61B 5/02233* (2013.01);
(Continued)

(58) Field of Classification Search
CPC ............ A61B 5/02108; A61B 5/02233; A61B 5/0225; A61B 5/6824; A61B 5/7203; A61B 5/0235
(Continued)

(56) References Cited

U.S. PATENT DOCUMENTS 4,651,748 A * 3/1987 Vinogradov ........... A61B 5/022
600/493
4,669,485 A * 6/1987 Russell .................. A61B 5/021
600/492
(Continued)

*Primary Examiner* — Navin Natnithithadha
(74) *Attorney, Agent, or Firm* — WRB-IP LLP

(57) ABSTRACT

An apparatus for an accurate automated non-invasive measurement of blood pressure waveform using brachial (occlusion) cuff pressurized above systolic pressure and using differential pressure sensor. The methodology involves measurement in suprasystolic mode and in utilization and construction of the device followed by algorithms for processing and analysis of measured blood pressure pulse waves and assessment of hemodynamic parameters of human cardiovascular system. The device includes an electro-pump connected to the collar device, a differential pressure sensor, pressure senor A, pressure sensor B, valve, closing a valve and the air reservoir. The cuff is wrapped around a person's arm. The values of the instantaneous pressure in the pneumatic portion of the device are converted into an electric signal by the pressure sensor A, pressure sensor B and the differential pressure sensor. These signals are then filtered using a set of passive RC elements for filtering out high frequency interference, and fed to the microprocessor with a computing unit, analog to digital converter. The sampling frequency is sensed signal at least 200 Hz. The control
(Continued)

algorithm in the microprocessor, according to signals from the pressure sensor A further controls the course of cuff pressurization, controls the control valve, and finally determines the closing and opening of the closing valve. A microprocessor further controls a display and the data may be transmitted to the PC.

6 Claims, 1 Drawing Sheet

(51) Int. Cl.
    *A61B 5/021*     (2006.01)
    *A61B 5/022*     (2006.01)
    *A61B 5/00*     (2006.01)
(52) U.S. Cl.
    CPC .......... *A61B 5/6824* (2013.01); *A61B 5/7203* (2013.01); *A61B 5/0235* (2013.01)
(58) Field of Classification Search
    USPC ........................................ 600/485, 490–499
    See application file for complete search history.

(56) References Cited

U.S. PATENT DOCUMENTS

| | | | | |
|---|---|---|---|---|
| 4,718,426 A * | 1/1988 | Russell | ................. | A61B 5/021 600/490 |
| 4,718,427 A * | 1/1988 | Russell | ................. | A61B 5/021 600/490 |
| 4,718,428 A * | 1/1988 | Russell | ................. | A61B 5/021 600/490 |
| 4,889,133 A * | 12/1989 | Nelson | ............... | A61B 5/02225 600/494 |
| 5,570,694 A * | 11/1996 | Rometsch | .......... | A61B 5/02225 137/487.5 |
| 5,680,868 A * | 10/1997 | Kahn | .................... | A61B 5/021 600/493 |
| 8,840,561 B2 * | 9/2014 | Lane | .................. | A61B 5/02225 600/495 |
| 2012/0059267 A1 * | 3/2012 | Lamego | ................. | A61B 5/021 600/483 |
| 2012/0330112 A1 * | 12/2012 | Lamego | ................. | G06F 19/00 600/301 |
| 2013/0204139 A1 * | 8/2013 | Kashif | ................... | A61B 5/031 600/454 |
| 2014/0163402 A1 * | 6/2014 | Lamego | ............ | A61B 5/02141 600/493 |

* cited by examiner

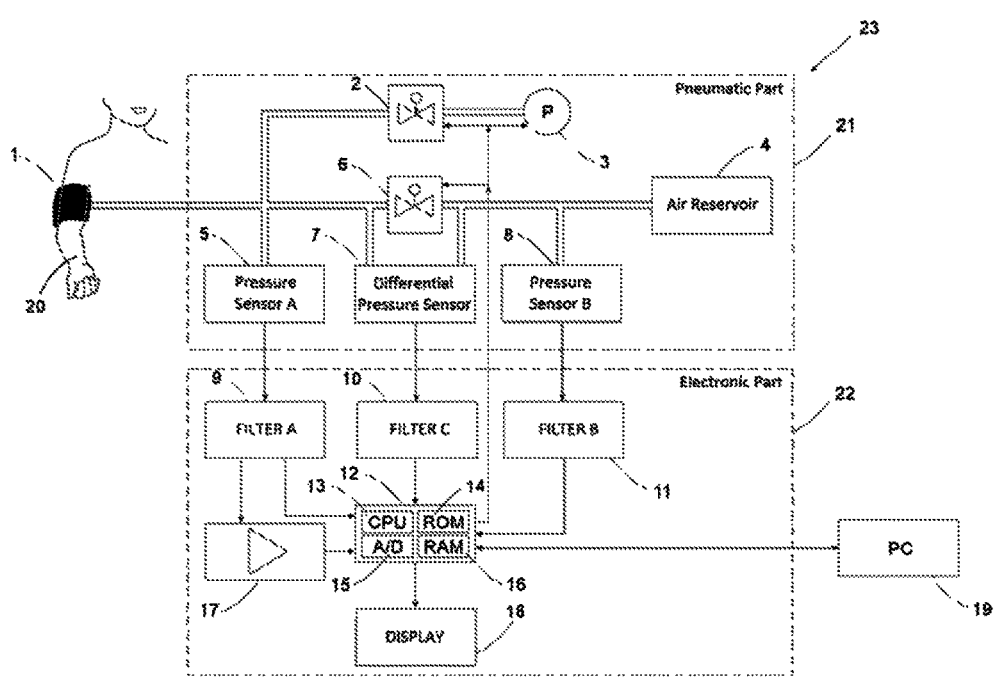

METHOD FOR AN ACCURATE AUTOMATED NON-INVASIVE MEASUREMENT OF BLOOD PRESSURE WAVEFORM AND APPARATUS TO CARRY OUT THE SAME

BACKGROUND AND SUMMARY

The present application claims priority to Czech Republic Patent Application PV 2016-6, filed Jan. 7, 2016, which is incorporated by reference. The technical solution concerns a method for accurate automated non-invasive measurement of blood pressure waveform and the apparatus to carry out the method. By using the device and the method, and based on measured signals processed by developed algorithms it is possible to effectively determine important hemodynamic parameters of cardiovascular system. This device is intended for use in human and veterinary medicine, especially in the investigation of the state of cardiovascular system, i.e. hemodynamic parameters of bloodstream.

Devices for determination of hemodynamic parameters of cardiovascular system based on measurement of pressure waves are widely used in human medicine. They enable to determine many advanced hemodynamic parameters that enable complex assessment of cardiovascular system including pulse wave velocity (PWV), augmentation index (AIx) that servers as basic parameters for assessment of Arterial Stillness (AS) and risk of development and progression of arteriosclerosis and associated comorbidities.

Superior and most precise method for assessment of above-mentioned parameters still remains invasive measurement by catheter introduced to aortic root. This is still invasive operating procedure associated with certain known health risks and high price. The examination can't be performed under ambulatory conditions and have to be performed by certified interventional cardiologist in specially equipped operating room for angiology including catheter and other equipment to perform this type of surgery.

Non-invasive substitution of the invasive method is described in patent U.S. Pat. No. 6,117,087 and uses contact pressure sensor and sophisticated mathematical models derived from limited amount of data measured of patients with indications of several cardiovascular diseases. Learning models under such circumstances introduces high infidelity into the method.

Another solution is described in Czech patent number 295119, where measurement of blood pressure pulse wave is accomplished by contact pressure sensor connected to differential pressure sensor that increases sensitivity of measured pressure curve. This solution enables to measure very small blood pressure pulse waves from the surface of pressurized arteries at radial arteries with option of PWV analysis using special setup of device and utilization of two sensors, while there is no constriction of measured artery by the device. Placement of the device at radial artery is main limitation of the method to assess central aortic pulse wave as well as brachial pulse wave. This is because of known physiological phenomenon that describes change of pattern and amplitude of pulse wave in a particular place if measured from the aortic root distally along arm compare to pulse wave measured in the aortic root. This phenomenon applied to the method suggests that the method has substantial inaccuracy as well.

Main disadvantages of devices that use contact pressure sensor (e.g. Sphygmocor CVMS by AtCor) are changes of sensed pulse wave that are introduced by movements of examiner (physician) and by patient during measurement. These changes generate inaccuracies. Another main disadvantage of the method is that measurement can't be carried out automatically and it needs trained medical personnel.

SphygmoCor XCEL (AtCor), Arteriograph (TensioMed) BP+ (Uscom) that determine hemodynamic parameters of cardiovascular system from pattern of suprasystolic pressure pulse waves doesn't offer solution of above-mentioned disadvantages. Measurement is carried out automatically and by using arm cuff for measurement of suprasystolic pressure pulse waves. As described in patent WO 2005077265 A1, these pulsations are sensed using suprasystolic pressure (preferred is a systolic pressure +35 mmHg) by standard pressure sensor used in devices for blood pressure measurement by standard oscilometric principle. Typical dynamic range of these sensors is usually min 40 kPa, and relative overpressure ~300 mmHg. Because of small amplitudes of suprasystolic pressure pulse waves device in patent WO 2005077265 A1 uses compensation filter ("reverse filter") that a circuit that compensates for pattern of the signal during measurement. This is method is burdened by inaccuracy and under discussion in scientific press—e.g. discussed in Validation of the Arteriograph working principle: questions still remain. Bram Trachet et al. Journal of Hypertension, 29:619-622, 2011. This remains similar also for patents US 2014135632 A1 and US 2010256507A1. Another disadvantage of above-mentioned devices is a complexity of mathematical models for assessment of hemodynamic parameters. These models are derived from limited set of the data and highly multivariate. They also need certain high amount of input parameters they use together with measured pressure pulse wave to be able to calculate a result. Other several sensors often supply these input parameters. Used models were often tested using limited sizes of study populations and limited types of cardiovascular diseases, which can introduce certain instabilities and inaccuracies into models and thus into the whole measurement system.

In an aspect of the present invention, accurate automated non-invasive measurement of blood pressure waveform according to the invention is provided. Its essence consists in the following method of measurement and in the following apparatus embodiment. The device consists of an electromechanical pump connected to an arm cuff, a differential pressure sensor, a pressure sensor A, a pressure sensor B, a control (decompression) valve, a closing valve and an air reservoir, with a minimal volume of 50 ml. Arm cuff is wrapped around the arm of the examined person and just tightened. Actual values of the pressures in the pneumatic components of the apparatus are converted into an electrical signal by the pressure sensor A, the pressure sensor B and the differential pressure sensor. These signals are then filtered using a set of passive RC low pass filters to remove high frequency interference, and thereafter through analog to digital converter (at least 12-bit) they are digitized and ready for further computer processing. The signal from pressure sensor A is after filtration amplified by an amplifier, approximately 50 to 100 times. The sampling frequency of the signal is at least 200 Hz. The control element, based on the current sensed values from the pressure sensor A and by casing the electromechanical pump, and the control and closing valves, controls and monitors the course of the cuff inflation during measurement. The control element (e.g. a microprocessor) senses, processes and evaluates the measured data that can be displayed directly on the display, or may be transferred to a PC for further processing.

In the first phase of measurement, the apparatus device according to the invention begins to inflate the arm cuffbladder via electromechanical pump, at a rate controlled by the control element, e.g. a microprocessor. The cuff inflation speed is gradually slowed down so that the pneumatic system reaches a specified value of suprasystolic pressure. Through the closing valve, which is located between the inputs of the differential pressure sensor, and which is at this phase of measurement in open position, is inflated the air reservoir, which serves to minimize pressure variations in the pneumatic system. During the controlled inflation of the pneumatic system, the processor continually evaluates oscillometric pulsations obtained by digitalization of filtered and amplified signal from the pressure sensor A. Based on measured oscillometric pulsations during cuff inflation and cuff pressure signal from unamplified pressure sensor A, the value of suprasystolic pressure is determined by the control element (e.g. a microprocessor). The value of suprasystolic pressure is at least 30 mmHg higher than a systolic pressure of measured person. Pneumatic system is inflated to the suprasystolic pressure by an electromechanical pump before starting the measurement of blood pressure waveform.

A necessary condition for quality measurement of the pulse pressure wave by the apparatus according to the invention is to achieve suprasystolic pressure in the cuff placed on the arm over the brachial artery. After reaching the suprasystolic pressure and its stabilization, i.e. the pressure drop in the pressure sensors A and B is less than 1 mmHg/min, there is a signal from the processor to trigger the closing valve, i.e. the valve is closed. This separates the inputs of differential pressure sensor, i.e. separation of the static cuff pressure from pressure with superimposed pressure pulsations. At output of the differential sensor with a range of hundreds of Pa—preferred±250 Pa or ±500 Pa, i.e. approx.±1.88 mmHg, respectively±3.75 mmHg, appears blood pulse wave signals—pressure pulsations, separated from the static pressure cuff. Next phase of measurement is suprasystolic pressure pulsations measurement. During this phase, the tightness in separate parts of a pneumatic system is monitored using the signals from the pressure sensors A and B. This procedure yields a signal that is up to 100 times more sensitive compare to existing methods of suprasystolic pressure pulsations measurement. This thus eliminates disadvantages of existing devices for the automatic measurement suprasystolic pressure pulsations, in particular the need of using a compensation filter or derived complex multivariate models.

After suprasystolic pressure pulsations measurement is finished, a control element (e.g. a microprocessor) opens the closing valve and by regulation (decompression) valve gradually releases the cuff pressure, and pressure throughout the whole pneumatic system. During the controlled deflation the oscillometric pulsations from pressure sensor A are measurement and therefore it is possible to measure blood pressure—systolic, diastolic, mean arterial, using standard oscillometric method.

System automatically determines actual heart rate of the person using analysis of measured data. Other hemodynamic parameters of cardiovascular system of examined person are automatically determined from the pattern of the signal, e.g. systolic and diastolic blood pressure of each heartbeat, pulse wave velocity (PWV), augmentation index (AIx), central aortic pressure, area under the curve and the maximum pressure amplitude, which reflects the instantaneous stroke volume, and others.

The measured pressure curve is accurate and corresponds to the brachial pulse wave otherwise invasively measured by a catheter placed in patient's arm. The apparatus according to the invention is accurate, portable, and inexpensive and is usable even in individuals with cardiovascular disease, or cardiovascular system status changes. To operate the device is simple and it is easy to learn. Patient themselves are able to perform the measurement after a short learning practice period. It allows carrying out measurements in outpatient settings, such as surgery cardiologists, internists and general practitioners, but also at home environment. The whole one trial of scanning procedure takes at maximum two minutes and it does not burden or harm the patient.

BRIEF DESCRIPTION OF THE DRAWINGS

The invention is illustrated using the attached drawing, wherein FIG. 1 is a block diagram of an exemplary apparatus according to the invention.

DETAILED DESCRIPTION

There is a block diagram of device 23 according to the invention in the FIG. 1. The device for non-invasive measurement of suprasystolic pressure pulsations of the invention implemented by a microprocessor 12 with a 24-bit A/D converter 15 with a sampling frequency of 200 Hz. Inflating the pneumatic part 21 of the device 23, including the occlusive cuff 1, which is located in the patient arm 20 and the air reservoir 4 of 100 ml volume, is carried out by electromechanical pump 3. Control (decompression) valve 2 is located between the inputs of the differential pressure sensor 7 and is controlled, as well as the process of inflating the pneumatic part 21, by computing unit 13 of the microprocessor 12, according to an algorithm stored in the program memory of the microprocessor (ROM) 14. Signals measured from the pressure sensor A 5, pressure sensor B 8 and the differential pressure sensor 7 are preprocessed using a filter A 9, filter B 10 and filter C 11—RC low pass filters to eliminate high frequency interference, and an amplifier of oscillometric pulsations 17 and are stored in the data memory (RAM) 16 of the microprocessor 12. Digitalized data can be transmitted to the PC 19 for additional processing and simultaneously displayed on the display 18. Electronic part 22 of the device 23, the differential pressure sensor 7, the pressure sensor A 5, pressure sensor B 8, the electromechanical pump 3, the control (decompression) valve 2 and the closing valve 6 are powered by batteries.

In the device for an accurate automated non-invasive measurement of blood pressure waveform using brachial (occlusion) cuff pressurized above systolic pressure and using differential pressure sensor. Methodology involves measurement in suprasystolic mode and in utilization and construction of the device followed by algorithms for processing and analysis of measured blood pressure pulse waves and assessment of hemodynamic parameters of human cardiovascular system. The device comprises an electro-pump (4) connected to the collar device (1), the differential pressure sensor (7), pressure sensor A (6), pressure sensor B (8), valve (2), closing a valve (6) and the air reservoir (4). Cuff (1) is wrapped around the arm persons under investigation (20). The values of the instantaneous pressure in the pneumatic portion (21) of the device (23) are converted into an electric signal by the pressure sensor A (6), pressure sensor B (8) and the differential pressure sensor (7). These signals are then filtered using a set of passive RC elements (9), (10), (11) for filtering out high frequency interference, and fed to the microprocessor (12) with a computing unit (13), analog to digital converter (15). The sampling frequency is sensed signal at least 200 Hz. The control algorithm in the microprocessor (12), according to signals from the pressure sensor A (6) further controls the course of cuff pressurization, controls the control valve (2), and finally determines the closing and opening of the closing valve (6). A microprocessor (12) further controls a display (18) and the data may be transmitted to the PC (19).

The device according to the invention finds an application in civilian use of individual care for non-invasive monitoring of hemodynamic parameters of the cardiovascular system and for a prognosis of cardiovascular diseases, in the area of medical care and postoperative monitoring of patients, but also in preventive medical care, and thereby preventing cardiovascular disease and its comorbidities.

What is claimed is:

1. A method for automated non-invasive measurement of blood pressure pulse waves, comprising:
   wrapping an arm cuff around an arm of a person to be examined person, the arm cuff being pneumatically connectable to and disconnectable from a pressurizable air reservoir via a closing valve;
   opening the closing valve;
   after opening the closing valve, inflating the arm cuff and pressurizing the cuff and the reservoir until a value of a suprasystolic pressure at least 30 mmHg higher than a systolic pressure of the person is reached in the arm cuff;
   closing the closing valve; and
   after closing the closing valve
      sensing suprasystolic pressure pulsations by detecting pressure differences an opposite sides of the closing valve,
      converting sensed suprasystolic pressure pulsations into electrical signals,
      filtering the electrical signals to eliminate high frequency interference and provide filtered electrical signals, and
      digitizing the filtered electrical signals for computer processing.

2. The method according to claim 1, comprising, after inflating the arm cuff, performing a controlled deflation of the arm cuff, and detecting oscillometric pulsation during the controlled deflation for measurements of systolic, diastolic and mean pressure using a standard oscillometric method.

3. A device for automated non-invasive measurement of blood pressure pulse waves of a person, comprising
   a pneumatic part comprising
      an arm cuff,
      a pressurizable air reservoir,
      a closing valve arranged in a conduit between the cuff and the reservoir for selectively pneumatically connecting the cuff and the reservoir to each other and pneumatically disconnecting the cuff and the reservoir from each other,
   an electromechanical pump connectable to the cuff and, the air reservoir via the conduit,
   a differential pressure sensor arranged to sense a pressure differential on opposite sides of the closing valve,
   a first pressure sensor arranged to sense a pressure drop in the cuff,
   a second pressure sensor arranged to sense a pressure drop in the reservoir,
   a control valve arranged between the pump and the conduit, and
   an electronic part comprising a control element comprising a computing unit, a program memory, a data memory, and an analog-digital converter, the electronic part being configured to
      open the closing valve,
      after opening the closing valve and the control valve, inflate the arm cuff via the pump and pressurize the cuff and the reservoir until a pressure higher than a systolic pressure of the person is reached in the arm cuff,
      close the closing valve, and
   after closing the closing valve
      sense suprasystolic pressure pulsations by detecting pressure differences on opposite sides of the closing valve,
      convert sensed suprasystolic pressure pulsations into electrical signals,
      filter the electrical signals to eliminate high frequency interference and provide filter electrical signals, and
      digitize the filtered electrical signals for computer processing.

4. The device according to claim 3, wherein a sampling frequency of signals in the control element is 180 Hz to 220 Hz.

5. The device according to claim 3, wherein the control element is configured to control the closing valve to pneumatically separate, after reaching a suprasystolic pressure at least 30 mmHg higher than a systolic pressure of the person is reached in the cuff and the reservoir, pressure in the reservoir from pressure superposed suprasystolic blood pressure pulsations in the cuff.

6. The device according to claim 3, wherein the first and second pressure sensors are arranged to monitor pressure drop in the pneumatic part during measurement of suprasystolic pressure pulsations.

* * * * *